US00PP16210P3

(12) United States Plant Patent
Egger

(10) Patent No.: US PP16,210 P3
(45) Date of Patent: Jan. 24, 2006

(54) ***HEUCHERA* PLANT NAMED 'LIME RICKEY'**

(50) Latin Name: *Heuchera hybrida*
Varietal Denomination: Lime Rickey

(75) Inventor: Janet Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 137 days.

(21) Appl. No.: 10/871,417

(22) Filed: Jun. 18, 2004

(65) Prior Publication Data

US 2005/0283871 P1 Dec. 22, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
*Assistant Examiner*—Annette H Para
(74) *Attorney, Agent, or Firm*—Klarquist Sparkman, LLP

(57) ABSTRACT

A new and distinct hybrid of *Heuchera* plant characterized by lime green wavy foliage and vigor.

1 Drawing Sheet

Botanical classification: *Heuchera hybrida.*
Cultivar name: 'Lime Rickey'.

The present invention relates to a new and distinct cultivar of *Heuchera hybrida* and given the cultivar name of 'Lime Rickey'. *Heuchera* is in the family Saxifragaceae. *Heuchera* 'Lime Rickey' originated from a cross between *Heuchera* 'Amber Waves', (U.S. Plant Pat No. 13,348) as the seed parent, and *Heuchera* 'Huntsman', an unpatented plant as the pollen parent. Given its ornamental foliage and flower form it is known that *Heuchera micrantha, H. americana, H. brizoides,* and *H. sanguinea* are in its parentage.

This new *Heuchera* is distinguished by:

1. Lime green, wavy foliage summer through winter. Lime green rather than green is new and unique color for *Heuchera* species.
2. Gold spring foliage.
3. Small white flowers on medium length flowering stems.
4. Excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
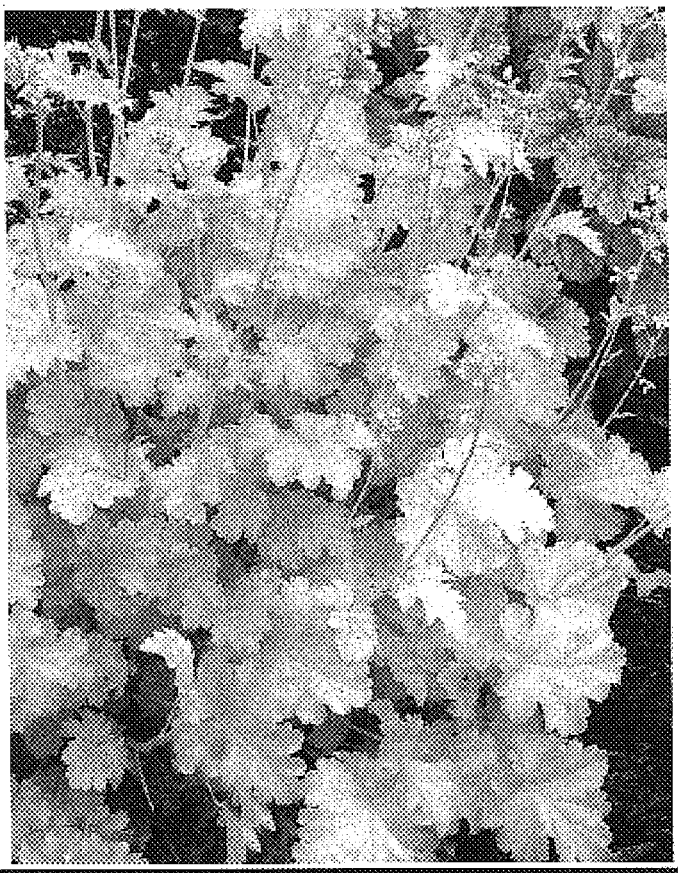
FIG. 1 shows *Heuchera* 'Lime Rickey' in bloom, growing in a one-gallon container in the shade house in summer in Canby, Oreg.
Figure 2:
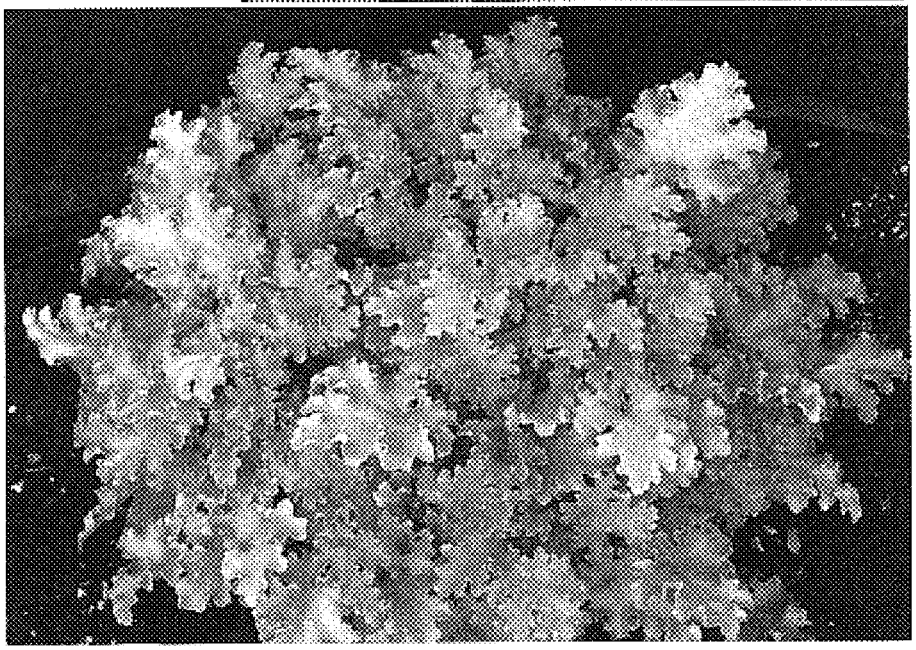
FIG. 2 shows *Heuchera* 'Lime Rickey' growing in the ground in the shade house in spring in Canby, Oreg.

The following is a detailed description of the new *Heuchera* cultivar based on observations of a two-year-old specimen grown in the ground in a shade house in Canby, Oreg. The color descriptions are all based on The Royal Horticultural Society Colour Chart.

Botanical classification: *Heuchera hybrida.*
Cultivar name: 'Lime Rickey'.
Parentage: *Heuchera hybrida* 'Amber Waves' U.S. Plant Pat No. 13,348 (seed parent)×*Heuchera hybrida* 'Huntsman' (pollen parent).

Plant:
- *Form.*—Basal rosette, herbaceous perennial.
- *Hardiness.*—USDA Zone 4 to 9.
- *Size.*—20 cm tall and 48 cm wide.
- *Habit.*—Mounding.

Leaf:
- *Type.*—Simple.
- *Arrangement.*—Rosette.
- *Shape.*—Ovate, irregular due to undulations.
- *Lobing/division.*—5 lobes, with 1 to 2 shallow secondary lobes.
- *Venation.*—Palmate.
- *Margins.*—Crenate and undulate.
- *Apex.*—Mucronulate.
- *Base.*—Cordate, lobes overlapping at the base.
- *Blade size.*—5.5 to 7.7 cm long and 4.5 to 7 cm wide.
- *Vestiture.*—Sparsely glandular both sides.
- *Aspect.*—Matte.
- *Texture.*—Thin, leathery.
- *Petiole length.*—11 to 13 cm.
- *Petiole vestiture.*—Glandular hairs of various sizes.
- *Petiole color.*—Yellow Green 154C to 145C.
- *Leaf color.*—Spring abaxial — Yellow 9A. Spring adaxial — Yellow Orange 14D. Summer through winter abaxial — Lime, Yellow Green 145A. Summer through winter adaxial — Yellow Green 145B.

Inflorescence:
*Size.*—5 to 7 cm wide and 7 to 20 cm long.
*Type.*—Thryse.
*Number of flowers.*—80 to 150 per thyrse.
*Number of thyrse.*—15.
*Peduncle.*—With 2 to 4 petiolate cauline leaves, ovate, blades 2 to 5 cm long and 1 to 4 cm wide with a lobed and incised margin. Height — 41 to 58 cm. Diameter — 0.4 cm near base. Color — Yellow Green 151C. Vestiture — Glandular.
*Branching.*—3 times.
*Pedicel.*—Length — Variable. Vestiture — Glandular hairs. Color — Yellow Green 151A.
*Bloom period.*—May in Canby, Oreg.

Flower bud:
*Size.*—0.25 cm wide and 0.4 cm long.
*Description.*—Glandular puberulent, ovoid.
*Color.*—Cream, Yellow White 158A.

Flower:
*Type.*—Perfect, zygomorphic.
*Shape.*—Campanulate.
*Size.*—0.4 cm long and 0.3 cm wide.
*Petal count.*—5, inconspicuous.
*Petal color.*—White 155D.
*Petal shape.*—Spatulate with a clawed base, reflex slightly.
*Petal size.*—0.35 cm long.
*Calyx.*—5 lobes, divided ⅓ way to the base, with glandular hairs.
*Calyx size.*—0.4 cm long and 0.3 cm wide.
*Calyx and flower color.*—White 155A with Greyed Orange 168A spots near base.
*Stamen number.*—5.
*Pistil color.*—White 155B.
*Pistil color.*—White 155B.
*Anther color.*—Orange 24B.
*Pollen color.*—Orange 24A.
*Fragrance.*—None.
*Lastingness.*—Each thryse blooms for about 2 weeks on the plant.

Fruit:
*Type.*—Two-beaked ovoid capsule.
*Fertility.*—Good.
*Color.*—Brown 200D.

Seed:
*Shape.*—Linear.
*Size.*—2 mm. long.
*Color.*—Black. RHS 202A.

Disease and pest tolerance: Shows excellent disease resistance to powdery mildew, the common problem of *Heuchera.* Susceptible to *Heuchera* rust and root weevils.

COMPARISON TO SIMILAR *HEUCHERAS*

There is no other lime-colored foliage *Heuchera* on the market. Compared to its seed parent *Heuchera* 'Amber Waves' (U.S. Plant Pat. No. 13,348), this new variety has lime green rather than amber colored foliage and white rather than creamy pink colored flowers. Compared to its pollen parent, *Heuchera* 'Huntsman', the new variety has lime green, wavy leaves with white flowers rather than green leaves with dark centers, no wavy leaf margins, and pink flowers.

I claim:

1. A new and distinct hybrid of *Heuchera* plant characterized by lime green wavy foliage and vigor.

* * * * *